a second pressure plate interposed between the driving plate and said first pressure plate and supported for rotation with the flywheel;

a first driven plate interposed between said first driving surface and said first pressure plate;

a second driven plate interposed between said second driving surface and said second pressure plate;

spring means interposed between said first and second pressure plates and acting on each of said pressure plates to exert a clamping load on each driven plate;

and a plurality of release mechanisms, each release mechanism comprising:

a lever, pivotably connected to the driving plate about a respective first pivot axis on the other side of the driving plate to said first driving surface;

a first link, pivotably connected to the lever about a respective second pivot axis;

an abutment on said first link;

adjustment means on the lever to contact said abutment to move said first link with the lever when the lever is pivoted in one direction;

an abutment member, pivotably connected to said first link about a respective third pivot axis parallel to said first pivot axis and operably connected to said second pressure plate to move said second pressure plate away from said second driving surface when the lever is pivoted in said one direction;

a second link operatively connected to the lever and said first pressure plate to move said first pressure plate away from said flywheel when the lever is pivoted in said one direction;

and means on the lever for engagement with a clutch release bearing which is operable to rotate said lever in said one direction.

2. The friction clutch of claim 1 wherein said first and second pivot axes in each release mechanism are coincident.

3. The friction clutch of claim 2 wherein each release mechanism comprises a single pivot pin which connects said first link and said lever to said driving plate.

4. The friction clutch of claim 1 wherein said abutment member comprises a third link.

5. The friction clutch of claim 1 wherein said adjustable abutment comprises a setscrew.

6. The friction clutch of claim 1 wherein each of said third axes lies in a plane which is nearer said second driving surface than a plane containing each of said first axes.

7. The friction clutch of claim 1 wherein said spring means comprises a single Belleville spring.

* * * * *

ACTIVE DERIVATIVES OF METHYLAMINE, THERAPEUTIC COMPOSITIONS CONTAINING THE SAME AND PROCESSES FOR PREPARING THE SAID DERIVATIVES AND COMPOSITIONS

The present invention relates to pharmacologically active derivatives of methylamine and their pharmaceutically acceptable acid addition salts as well as to pharmaceutical and veterinary compositions containing the said derivatives and salts.

The invention also concerns processes for preparing the derivatives of the invention and for the preparation of compositions containing them.

The pharmacologically active compounds with which the invention is concerned correspond to the following general formula:

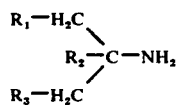

wherein $R_1$ and $R_3$ each represent a hydrogen atom or a sraight-or branched-chain alkyl, alkenyl or alkynyl radical containing from 1 to 6 carbon atoms, $R_2$ represents a straight-or branched-chain alkyl, alkenyl or alkynyl radical containing from 2 to 7 carbon atoms with the proviso that when $R_2$ represents an alkenyl radical of the formula CH=CH—R4 or an alkynyl radical of the formula C≡C—R4, in which $R_4$ represents a hydrogen atom or a straight-or branched-chain alkyl radical of 1 to 5 carbon atoms, $R_1$ and $R_3$ each represent an atom of hydrogen or an alkyl radical, $R_1$, $R_2$ and $R_3$ being such that no compound of formula I possesses more than 13 carbon atoms.

The invention also relates to the pharmaceutically acceptable acid addition salts of the compounds of formula I such as the acid addition salts obtained with an inorganic acid, for example, hydrochloric acid, or with an organic acid in which the free carboxyl is attached to a saturated or unsaturated aliphatic radical, or an aromatic or aralkyl radical which may optionally contain a second carboxyl group such as, for example, fumaric acid.

Another object of the present invention is a pharmaceutical or veterinary composition containing as essential active ingredient at least one of the methylamine derivatives defined in formula I or a pharmaceutically acceptable acid addition salt thereof in association with an appropriate pharmaceutical carrier or excipient therefor.

A further object of the invention is to provide a process for preparing pharmaceutical or veterinary compositions whereby at least one methylamine derivative of formula I or a pharmaceutically acceptable acid addition salt thereof is placed in association with an appropriate pharmaceutical carrier or excipient.

As will be described in greater detail further on, it has been found that the methylamine derivatives of formula I and their pharmaceutically acceptable acid addition salts possess pharmacological properties likely to render them particularly useful in the treatment of Parkinson's disease and for correcting extra-pyramidal disturbances provoked by neuroleptics.

In consequence, another object of the invention is to provide a method of treating Parkinson's disease and of correcting extra-pyramidal disturbances provoked by neuroleptics, which method comprises the administration to the patient so affected of at least one compound of formula I or a pharmaceutically acceptable acid addition salt thereof.

Daily dosage will preferably be between 10 to 60 mg of active principle for a human being weighing 60 kg.

Amongst the compounds of formula I, a certain number may be considered as novel.

The invention relates, in consequence, to the new derivatives of methylamine listed below, all of which are included in formula I:

1,1-Diethyl-n-butylamine
1,1-Di-n-propyl-n-propylamine
1-Ethyl-1-isobutyl-n-butylamine
1,1,3-Trimethyl-n-heptylamine
1,1-Dimethyl-3-ethyl-n-hexylamine
1,3-Dimethyl-1-ethyl-n-hexylamine
1,3-Dimethyl-1-n-propyl-n-pentylamine
1-Methyl-1-isobutyl-n-pentylamine
1-Methyl-1-n-propyl-n-hexylamine
1-n-Propyl-1-isobutyl-n-butylamine
1,1-Diisobutyl-n-butylamine
1-Ethyl-1-n-propyl-n-pentylamine
1-n-Propyl-1-isobutyl-n-butylamine
1-n-Propyl-1-tert-butyl-n-butylamine
1,1-Di-n-propyl-2-propyn-1-ylamine
1,1-Diethyl-2-pentyn-1-ylamine
1,1-Di-n-propyl-2-pentyn-1-ylamine
1,1-Di-n-propyl-3-butyn-1-ylamine
1,1-Diethyl-2-penten-1-ylamine
1,1-Di-n-propyl-2-penten-1-ylamine and the pharmaceutically acceptable acid addition salts of each of these new methylamine derivatives, together with the acid fumarate of 1,1-di-n-propyl-n-butylamine.

There are, however, a certain number of the compounds of the invention which are already known. In this connection may be cited, for example:

1,1-Di-(2-propen-1-yl)-3-buten-1-ylamine
or triallylmethylamine, 1,1-diallyl-n-butylamine and 1,1-diallyl-n-pentylamine which are described in the J. Amer. Chem. Soc., 65, 87 (1943)

1,1,3,3-Tetramethyl-n-butylamine published in the J. Amer. Chem. Soc., 70, 4048 (1948)

1-Methyl-1-ethyl-2-pentyn-1-ylamine
1-Methyl-1-ethyl-2-heptyn-1-ylamine
1-Methyl-1-ethyl-n-pentylamine
1-Methyl-1-ethyl-n-propylamine
1-Methyl-1-ethyl-2-propen-1-ylamine all of which are described in the J. Amer. Chem. Soc., 75, 4297 (1953)

1,1-Diethyl-2-propyn-1-ylamine
1,1-Dimethyl-2-propyn-1-ylamine
1,1-Diethyl-n-propylamine which are already on the market.

However, as far as is known, no therapeutic activity has ever been attributed to these known compounds.

Similarly, Tri-n-propylmethylamine or 1,1-di-n-propyl-n-butylamine, and Tri-n-butylamine or 1,1-di-n-butyl-n-pentylamine have been described by SPERBER et al. in the J. Amer. Chem. Soc., 71, 3352 (1949), where they are presented as being "less spasmolytic and more toxic than the corresponding trialkylethylamines". Here it is more a question of a musculotropic antispasmodic activity as pointed out in the reference in question.

in which $R_4$ has the meaning given above and Hal has the same meaning as in formula V to obtain the required compound of formula I which may then be reacted with an organic or inorganic acid to provide a pharmaceutically acceptable acid addition salt of the said compound.

The compounds of formula I in which $R_1$ and $R_3$ each represent an atom of hydrogen or an alkyl radical and $R_2$ represents an alkenyl radical of the formula $CH=CH-R_4$ in which $R_4$ has the same meaning as in the definition of formula I may be prepared by hydrogenating in an appropriate solvent such as, for example, heptane, and in the presence of a Lindlar catalyst, an amine of the general formula:

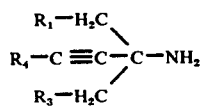
VIII in which $R_1$, $R_3$ and $R_4$ have the meaning given above, to provide the required compound of formula I which may then be reacted with an organic or inorganic acid to obtain a pharmaceutically acceptable acid addition salt of the said compound.

The operation of hydrogenation is preferably carried out at a temperature between 30° C and 60° C and generally at about 50° C.

The compounds of formula II may be prepared in various ways, namely:

a. when A represents the radical $N=C=O$:
either by reacting an acetamide derivative of the general formula:

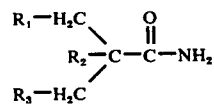
IX in which $R_1$, $R_2$ and $R_3$ have the same meaning as in formula II with chlorine or bromine in an alkaline medium such as, for example, in an aqueous solution of sodium or potassium hydroxide, or by reacting an acetic acid derivative of the general formula:

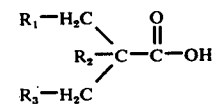
X in which $R_1$, $R_2$ and $R_3$ have the same meaning as in the compounds of formula II above with a chlorinating agent such as, for example, thionyl or oxalyl chloride, to obtain the corresponding acyl chloride which is then treated with an alkali metal azide such as, for example, sodium azide, which provides the required compound of formula II, or following another process, by heating a compound of formula X directly with hydrogen azide in an acid medium, for example, sulphuric acid, to obtain the desired compound of formula II.

In this latter case, the isocyanate thus formed is immediately converted by hydrolysis to the corresponding amine of formula I b. When A represents the radical

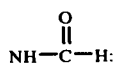

by heating a tertiary alcohol of the general formula:

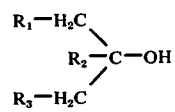
XI in which $R_1$, $R_2$ and $R_3$ have the same meaning as that given for the above compounds of formula II, with an alkaline cyanide such as, for example, sodium or potassium cyanide in the presence of an acid such as, for example, sulphuric acid.

The compounds of formula IX can be obtained by reacting anhydrous ammonia with the corresponding acids of formula X or preferably with the halides of these acids. The acids can be prepared from the alcohols of formula XI and formic acid in a sulphuric acid medium.

The compounds of formula XI are either known compounds or can be prepared in accordance with known procedures such as, for example, by reacting an organo-lithium compound with an appropriate ketone in an anhydrous ether medium such as, for example, tetrahydrofuran.

The compounds of formula V are either known products or can be prepared by the method described in the J. Org. Chem. 1961, 26, 725, i.e. by treating a 1,1-dialkyl-1-ethynyl-carbinol with cuprous chloride and hydrochloric acid in the presence of copper-bronze powder and calcium chloride. The 1,1-dialkyl-1-ethynyl-carbinols mentioned above are either known products, having been described in the Annales de Chimie, 1924, 10 (I), p 366, or can be prepared by known procedures described, for example, in Organic Syntheses Collective, Vol. III, p 416. The products of formula VI may be prepared in liquid ammonia through the action of an alkali metal such as, for example, sodium, on the corresponding 1,1-dialkyl-1-ethynyl-methylamine which is, in fact, a compound covered by formula I. The compounds of formula VIII are also included within the scope of formula I.

It has been discovered that the methylamine derivatives of formula I possess valuable pharmacological properties which are likely to render them useful in human and veterinary therapy.

In particular, it has been found that the compounds of the invention present central noradrenergic and central dopaminergic properties. These latter properties manifest themselves by an inhibitory action on reserpine-induced and neuroleptic-induced catatonia and catelepsy.

Pharmaclogical trials performed with the compounds of the invention have shown that tri-n-propylmethylamine hydrochloride or 1,1-di-n-propyl-n-butylamine hydrochloride possesses a marked degree of activity. However, it was surprisingly and quite unexpectedly, observed that 1,1-di-n-propyl-n-butylamine acid fumarate presents a degree of activity which is even markedly greater than that of the corresponding hydrochloride. It was, in fact, observed that 1,1-di-n-propyl-n-butylamine acid fumarate is from 20 to 40 percent more active than the corresponding hydrochloride in tests involving reserpine-induced and neuroleptic-induced catatonia.

Furthermore, at doses which completely suppress neuroleptic-induced catatonia and catalepsy, it was observed that the compounds of the invention do not influence the anti-amphetamine effects of the neuroleptics in the rat and their anti-apomorphine effects in the dog. Furthermore, the compounds of the invention have no emetic action in the dog at any doses and are not cholinolytic agents.

These pharmacological properties taken as a whole are likely to render the compounds of formula I useful in treating Parkinson's disease as well as for correcting extra-pyramidal disturbances provoked by neuroleptics.

Parkinson's disease is a chronic and progressive affection characterized in particular by a dopamine deficiency in the thalamus and the caudate and lenticular nuclei, with akinesia, rigidity and tremor as visible symptoms.

Many active drugs have already been proposed for combating Parkinson's syndrome. Most of these products are central anti-cholinergic agents with peripheral anti-cholinergic effects. These compounds are of natural origin, such as, for example atropine or are obtained synthetically as, for example, diethazine, benztropine or trihexyphenidyl.

However, these drugs may present undesirable side-effects, due in most cases to their peripheral anti-cholinergic properties, such side-effects taking the form, for example, of dryness of the mouth, difficulty in optical accommodation, tachycardia, constipation and retention of urine. These products will thus be contraindicated in cases of glaucoma and hypertrophy of the prostate.

L-Dopa or levodopa, a precursor of dopamine, has also been proposed in parkinsonism. However, in view of its partial destruction in the digestive system, L-dopa must be administered at very high doses, which very often induce undesirable side-effects. The most serious of these side-effects are cardiovascular in nature and in particular take the form of disturbances of cardiac rhythm and orthostatic hypotension. Patients treated with L-dopa must, therefore, not present contraindications on the cardiac plane.

Recently, amantadine i.e. 1-amino-adamantane has been proposed for antiparkinsonian therapy. This product, which stimulates the liberation of dopamine is very active but produces several undesirable side-effects and also decreases in activity after a certain length of time.

For this reason, it is very difficult for the doctor to select amongst the various antiparkinsonian drugs, that which will be effective for the case under treatment. Each patient must be considered as an individual case. All the known methods of treating Parkinson's disease are symptomatic and, in spite of the medication used, the disease continues to progress. The treatment of parkinsonism requires the successive use of one or more therapeutic substances and it is often necessary to institute therapeutic cycles. Frequently, two antiparkinsonian agents must be simultaneously administered, the first being considered as the basic drug and the second as an auxiliary or additional drug. Furthermore, since treatment is of long duration the alternating use of different products is necessary.

The search for new antiparkinsonian agents is therefore of primary importance. From this point of view, the compounds of formula I will constitute valuable additions to antiparkinsonian therapy, since at present there is no ideal agent for the treatment of this disease as explained in detail hereabove.

The compounds of the invention will consequently constitute valuable additions to the therapeutic arsenal at the disposal of the doctor and will provide useful replacement medication for any drug which has become ineffective for any reason such as a change in the state of the patient or habituation.

Although the pharmacological spectrum of the compounds of the invention is very similar to that of amantadine, pharmacological trials performed with the compounds of formula I have revealed marked differences in comparison with amantadine. For example, when comparing the doses of the compounds of the invention and of amantadine which have a certain degree of activity, it has been observed that the active dose in question is always proportionally farther from the toxic dose in the case of the compounds of the invention than in the case of amantadine. In other words, the safety margin offered by the compounds of the invention is superior to that of amantadine. Other differences which are particularly evident have been observed with the preferred compound of the invention, namely:

tri-n-propylmethylamine or 1,1-di-n-propyl-n-butylamine in basic form or in the form of a pharmaceutically acceptable acid addition salt such as the hydrochloride or the acid fumarate.

For example, on the cardiovascular plane, it has been observed that the preferred compound of the invention does not cause any undesirable effect on the electrocardiogram whereas a dose of 5 mg/kg of amantadine injected into the dog provokes cardiac arrhythmia due to ventricular extrasystoles. It has also been found that the preferred compound of the invention does not potentiate the peripheral effects of norepinephrine and is not a ganglioplegic agent while tests performed with amantadine have demonstrated that this compound potentiates the peripheral adrenergic effects and furthermore exerts a ganglioplegic action.

The preferred compound of the invention which does not present these undesirable side-effects observed with amantadine will not therefore induce cardiac disturbances or disorders of arterial pressure.

As mentioned above, certain types of antiparkinsonian agents such as diethazine, benztropine etc. frequently provoke undesirable side-effects of an anticholinergic nature (dryness of the mouth, difficulty in optical accomodation etc.).

The preferred compound of the invention being devoid of anti-cholinergic activity does not present these disadvantages.

Similarly, the preferred compound of the invention as it is devoid of emetic properties and of undesirable side-effects on the electrocardiogram, will not provoke vomiting or cardiac arrhythmia which are two frequent side-effects of L-dopa.

Pharmacological trials have been performed with a view to determining the various properties of the compounds of the invention which, taken together, are capable of rendering the said compounds useful in the treatment of Parkinson's disease and for the correction of extra-pyramidal disturbances induced by neuroleptics.

I. Inhibition of reserpine-induced and neuroleptic-induced catatonia (dopaminergic properties)

1. Inhibition of reserpine-induced catatonia

After sufficient doses of reserpine have been administered to the rat, a series of symptoms occur, more particularly ptosis, catatonia and a drop in central temperature. These symptoms are caused by the depletion of the intragranular reserve pool of biogenetic amines at the synaptic terminals.

The antidepressants of the tricyclic type as well as the inhibitors of monoamine oxydase (I.M.A.O.) antagonize more particularly the appearance of ptosis and the drop in central temperature. On catatonia, the action of such compounds is not non existent but is considerably less marked.

As against this, the synthetic antiparkinsonian agents principally influence catatonia while their activity on ptosis and hypothermia is non existent or weaker.

An oral dose of the compound to be studied in aqueous solution was administered to batches of 10 male rats of the OFA strain weighing about 150 to 200 g. Thirty minutes later a dose of 5 mg/kg of reserpine was given by intraperitoneal route. Three hours after the injection of reserpine, the animals were suspended by the four paws to a horizontally stretched wire fixed at 15 cm from the ground. The catatonic animals were those which maintained the position so given for at least 30 seconds. Each animal which maintained the position so given received the score of 1 and those which did not maintain the said position were given the score of 0. The maximum score was therefore 10 per batch. An identical trial was undertaken with control animals which received reserpine but none of the compounds being studied.

The following compounds of formula I were tested in comparison with amantadine in accordance with the process indicated hereabove. These compounds were preferably studied in the form of a pharmaceutically acceptable acid addition salt such as the hydrochloride or the fumarate.

1,1-Di-n-propyl-n-butylamine (Compound 1)
1-Ethyl-1-n-propyl-n-butylamine (Compound 2)
1-Ethyl-1-isobutyl-n-butylamine (Compound 3)
1-Ethyl-1-n-propyl-n-pentylamine (Compound 4)
1-n-Propyl-1-isobutyl-n-butylamine (Compound 5)
1,3-Dimethyl-1-n-propyl-n-pentylamine (Compound 6)
1,3-Dimethyl-1-ethyl-n-hexylamine (Compound 7)
1-Methyl-1-isobutyl-n-pentylamine (Compound 8)
1-Methyl-1-n-propyl-n-hexylamine (Compound 9)
1,1-Dimethyl-n-octylamine (Compound 10)
1,1-Di-(2-propen-1-yl)-3-buten-1-ylamine (Compound 11)
1,1-Di-n-butyl-n-pentylamine (Compound 12)
1,1,3-Trimethyl-n-heptylamine (Compound 13)
1,1-Diethyl-n-butylamine (Compound 14)
1,1-Diethyl-n-propylamine (Compound 15)
1,1-Dimethyl-n-propylamine (Compound 16)
1,1-Dimethyl-3-ethyl-n-hexylamine (Compound 17)
1,1-Diisobutyl-n-butylamine (Compound 18)
1-n-Propyl-1-isopropyl-n-butylamine (Compound 19)
1-n-Propyl-1-tert-butyl-n-butylamine (Compound 20)
1,1-Di-n-propyl-2-propyn-1-ylamine (Compound 21)
1,1-Diethyl-2-pentyn-1-ylamine (Compound 22)
1,1-Diethyl-2-penten-1-ylamine (Compound 23)
1,1-Di-n-propyl-2-pentyn-1-ylamine (Compound 24)
1,1-Di-n-propyl-2-penten-1-ylamine (Compound 25)
1,1-Di-n-propyl-3-butyn-1-ylamine (Compound 26)

The results obtained with the compounds of formula I listed hereabove as well as with amantadine are given in Table I hereunder. These results are expressed in the following manner:

0: represents 0% inhibition of catatonia in comparison with the controls (namely a score of 10 per studied batch).
1: represents 20 to 30% inhibition of catatonia in comparison with the controls (namely a score of 7 to 8 per studied batch).
2: represents 50% inhibition of catatonia in comparison with the controls (namely a score of 5 per studied batch)
3: represents 70 to 80% inhibition of catatonia in comparison with the controls (namely a score of 2 or 3 per studied batch).
4: represents 100% inhibition of catatonia in comparison with the controls (namely a score of 0 per studied batch).

Table I

| Compound | Dose administered in mg/kg | Inhibition of reserpine-induced catatonia |
|---|---|---|
| 1 | 5 | 4 |
| 2 | 5 | 1 |
| 3 | 20 | 3 |
| 4 | 20 | 3 |
| 5 | 20 | 2 |
| 6 | 20 | 1 |
| 7 | 20 | 1 |
| 8 | 20 | 1 |
| 9 | 20 | 1 |
| 10 | 20 | 1 |
| 11 | 20 | 1 |
| 12 | 20 | 1 |
| 13 | 25 | 1 |
| 14 | 50 | 3 |
| 15 | 50 | 1 |
| 16 | 50 | 1 |
| 17 | 11 | 1 |
| 18 | 12 | 2 |
| 19 | 6 | 3 |
| 20 | 6 | 2 |
| 21 | 30 | 2 |
| 22 | 60 | 1 |
| 23 | 60 | 1 |
| 24 | 20 | 1 |
| 25 | 6 | 3 |
| 26 | 30 | 1 |
| Amantadine | 100 | 4 |

These results show that Compound 1 which is the preferred compound of the invention is as active as amantadine but at a dose which is twenty times inferior to that of amantadine.

2. Inhibition of neuroleptic-induced catatonia

The blocking of dopaminergic receptors by neuroleptics in the extra-pyramidal system induces catatonia in the rat. Catatonia is differentiated from sedative properties by means of the test used hereabove for reserpine-induced catatonia. The same system of scoring was also employed in the present case.

An oral dose of the compound to be studied in aqueous solution was administered to batches of 10 male rats of the OFA strain weighing about 150 to 200 g. Thirty minutes later a dose of 12.5 mg/kg of prochlorperazine was given by intraperitoneal route. Three hours after the injection of this latter compound, catatonia was measured. An identical trial was also carried out with control animals which received prochlorperazine but none of the compounds under study.

The results obtained with the above listed compounds in comparison with amantadine are set out in the following Table II. The scoring system, used was that given hereabove in Table I.

Table II

| Compound | Dose administered in mg/kg | Inhibition of the neuroleptic-induced catatonia |
|---|---|---|
| 1 | 5 | 4 |
| 2 | 5 | 1 |
| 3 | 20 | 3 |
| 4 | 20 | 3 |
| 5 | 20 | 4 |
| 6 | 20 | 1 |
| 7 | 40 | 1 |
| 8 | 50 | 4 |
| 9 | 20 | 1 |
| 10 | 50 | 1 |
| 11 | 20 | 1 |
| 12 | 20 | 1 |
| 13 | 50 | 1 |
| 14 | 50 | 3 |
| 15 | 50 | 3 |
| 16 | 10 | 1 |
| 17 | 11 | 2 |
| 18 | 12 | 1 |
| 19 | 6 | 3 |
| 20 | 50 | 1 |
| 21 | 30 | 1 |
| 22 | 30 | 1 |
| 23 | 30 | 1 |
| 24 | 20 | 2 |
| 25 | 6 | 3 |
| 26 | 30 | 4 |
| Amantadine | 100 | 4 |

These results show that Compound 1 is also twenty times more active than amantadine in this test and that Compound 5 is five times more active than amantadine while Compound 8 is twice as active.

Furthermore Compound 1 at a dose as low as 1 mg/kg, provokes a 70% inhibition of the neuroleptic-induced catatonia.

The results mentioned in the above Tables I and II in connecton with Compound 1 were obtained with 1,1-di-n-propyl-n-butylamine in the form of its hydrochloride. In the form of its acid fumarate, 1,1-di-n-propyl-n-butylamine is from 20 to 40 percent more active as previously indicated. For example, a score of 4 was obtained in the tests involving reserpine-induced and neuroleptic-induced catatonia as described hereabove with only 3 mg/kg of 1,1-di-n-propyl-n-butylamine acid fumarate.

II. Acute toxicity

In the acute toxicity test the $LD_{50}$ was determined on mice by oral route using the method of Lichfield and Wilcoxon (J. Pharmacol. 1938, 2, 192–216). The compounds were administered in aqueous solution and the period of observation was 10 days after administration of the compound under study.

The following results were recorded in comparison with amantadine.

| Compound | $LD_{50}$ (in mg/kg) |
|---|---|
| 1 | 100 |
| 2 | 150 |
| 6 | >500 |
| 9 | 1750 |
| 12 | 500 |
| Amantadine | 1050 |

These results show that compounds of the invention are generally more toxic than amantadine. However, when a comparison is made between the $LD_{50}$ given hereabove and the effective dose to obtain inhibition of reserpine-induced or neuroleptic-induced catatonia, it is seen that such comparisons are always more favourable to the compounds of the invention than to amantadine. The index $LD_{50}/ED_{20-30}$ In this index, $ED_{20-30}$ represents the effective dose to obtain 20 to 30% inhibition of the catatonia, this value being represented by the FIG. 1 in Tables I and II.

The following results were registered:

| Compound | Index |
|---|---|
| 2 | 25 |
| 6 | >25 |
| 9 | 87 |
| 12 | 25 |

The corresponding index for amantadine is 1050/50 = 21, which shows that the compounds of the invention present greater advantages than amantadine.

Similarly, an index $LD_{50}/ED_{100}$ was determined, $ED_{100}$ representing the effective dose to obtain 100% inhibition of the catatonia.

This latter value is represented in Tables I and II by the FIG. 4.

The following results were recorded:

| Compound | Index |
|---|---|
| 1 | 20 |
| Amantadine | 10 |

These figures show that Compound 1 presents a total inhibitory action on reserpine-induced and neuroleptic-induced catatonia at a dose which is proportionally twice as far from the toxic dose as in the case of amantadine. Compound 1 possesses, consequently, a higher safety margin than that of amantadine.

In the case of 1,1-di-n-propyl-n-butylamine acid fumarate, the active dose is still farther removed from the toxic dose than in the case of Compound 1 as the corresponding index is 100/3 33.

Addition trials were carried out on rats with Compound 1 and amantadine. These trials involved catalepsy as evidenced by the crossing of the animal's homolateral paws. It was observed in these trials that 5 mg/kg of Compound 1 when administered by oral route 30 minutes before an intraperitoneal injection of prochlorperazine provoked complete inhibition of the catalepsy 3 hours after the injection of this latter substance. With regard to amantadine, a dose of 80 mg/kg was necessary to induce complete inhibition of the catalepsy.

The efficacy of Compound 1 in curative treatment was also demonstrated.

a. Suppression of reserpine-induced catatonia

Batches of 5 male rats of the OFA strain, weighing 150 to 200 g were given 5 mg/kg of reserpine by intraperitoneal route. One hour and 45 minutes later, namely when the animals were in a state of catatonia, an aqueous dose of the compound to be studied was administered by oral route to all the animals with the exception of the control group.

The progress of the catatonia was then noted following the scale used in the tests described hereabove.

The maximum score was thus 5 per batch which means that all the animals of the batch were considered to be still in a state of catatonia.

The following results were obtained with Compound 1 in comparison with amantadine:

Table III

| | Time after administration of reserpine | | | | | | |
|---|---|---|---|---|---|---|---|
| | 2h | 2h15 | 2h30 | 3h | 3h30 | 4h | 5h |
| Controls | 5 | 5 | 5 | 3 | 3 | 1 | 2 |
| Compound 1 2.5 mg/kg | 4 | 3 | 2 | 0 | 0 | 0 | 0 |
| Compound 1 5 mg/kg | 5 | 1 | 0 | 0 | 0 | 0 | 0 |
| Amantadine 80 mg/kg | 5 | 4 | 3 | 2 | 1 | 0 | 0 |

These figures show that at doses of 2.5 mg/kg and 5 mg/kg, by oral route, Compound 1 suppresses reserpine-induced catatonia more radpily than a dose of 80 mg/kg of amantadine administered under the same conditions.

Compound 1 is thus at least 32 times more active than amantadine with respect to reserpine-induced catatonia in curative treatment.

b. Suppression of neuroleptic-induced catatonia

Batches of 5 male rats of the OFA strain were given 12.5 mg/kg of prochlorperazine by intraperitoneal route. Fifty-five minutes later, an oral dose in aqueous solution of the compound to be studied was administered to all the animals with the exception of the control group. The progress of the catatonia was noted following the same scale as that used in the tests described above.

The following results were registered with Compound 1 as well as with amanadine:

Table IV

| | Time after administration of prochlorperazine | | | | | |
|---|---|---|---|---|---|---|
| | 1h30 | 2h30 | 3h | 3h30 | 4h | 5h |
| Controls | 4 | 4 | 4 | 3 | 1 | 1 |
| Compound 1 5 mg/kg | 3 | 0 | 0 | 0 | 0 | 0 |
| Amantadine 80 mg/kg | 5 | 2 | 1 | 0 | 0 | 0 |

These results show that under the conditions of curative treatment, a dose of 5 mg/kg of Compound 1 acts against neuroleptic-induced catatonia more rapidly than does a dose of 80 mg/kg of amantadine administered under the same conditions. In this test, Compound 1 is consequently at least 16 times more active than amantadine.

The toxico-pharmacological index, $LD_{50}/ED_{50}$, is again more favourable to Compound 1 than to amantadine, i.e. 20 for Compound 1 and only 13 for amantadine.

A test was also carried out in order to determine whether Compound 1 possessed cholinolytic properties.

For this purpose, the MAGNUS test (Arch. gen. Physio. 1904, 102) was used. This test consists in determining the dose of acetylcholine which, when added to the bath, provokes spasm of the isolated duodenum of the rat. The next step consists in determining the dose of the compound under study which, when added to the bath 30 seconds before the acetylcholine, reduces the spasm.

The following results were recorded with Compound 1 in comparison with atropine:

Table V

| | Doses in g/ml of bath | % of inhibition of the spasm |
|---|---|---|
| Acetylcholine | $0.5 \times 10^{-5}$ | — |
| Atropine | $0.1 \times 10^{-6}$ | 45 |
| | $0.2 \times 10^{-6}$ | 100 |
| Compound 1 | $0.2 \times 10^{-6}$ | 0 |
| | $0.1 \times 10^{-5}$ | 0 |

Table V-continued

| Doses in g/ml of bath | % of inhibition of the spasm |
|---|---|
| $0.1 \times 10^{-4}$ | 0 |
| $0.1 \times 10^{-3}$ | 0 |
| $0.2 \times 10^{-2}$ | 36 |
| $0.5 \times 10^{-2}$ | 60 |

These results show that Compound 1 is 20,000 to 25,000 times less active than atropine.

The cholinolytic activity "in vitro" of Compound 1 may thus be considered as virtually non-existent in comparison with that of atropine.

The extremely weak cholinolytic action of Compound 1 must necessarily occur at toxic doses.

The absence of cholinolytic properties of Compound 1 was verified "in vivo" at therapeutic doses.

For this purpose, the following test was performed with a view to determining the anti-tremorine properties of Compound 1.

When injected into mice, tremorine produces peripheral effects i.e. weeping, sweating, salivation and diarrhoea and central effects i.e. tremor and akinesia. Such effects are due to an increase in the amount of intracerebral acetylcholine and serotonine.

Male mice of the $OF_1$ strain weighing about 22 g were divided into batches of 10. Each batch received, by oral route, 50 mg/kg of the compound to be tested in aqueous solution. Thirty minutes later a dose of 10 mg/kg of tremorine was injected by intraperitoneal route and, at different times after this injection, note was taken of the cholinergic effects on each animal in accordance with the following scale:

| 0 | no action |
|---|---|
| 1 | slight action |
| 2 | average action |
| 3 | strong action |
| 4 | very strong action |

The results obtained with 5 mg/kg of Compound 1 and 40 mg/kg of amantadine were as follows:

With respect to the peripheral cholinergic effects i.e. salivation, sweating, and weeping, a score of 4 was registered for the control animals, 20, 30 and 40 minutes after the injection of tremorine for both 5 mg/kg of Compound 1 and 40 mg/kg of amantadine. Identical results were obtained with respect to the central cholinergic effects i.e. normal and provoked tremor.

These results show that Compound 1 and amantadine are devoid of antitremorine properties, which confirms the absence of cholinolytic properties in the case of Compound 1 at therapeutic doses.

Tests were also carried out with Compound 1 with a view to studying the influence of this compound on peripheral noradrenergic phenomena.

The following test was performed for this purpose:

A cat, anaesthetized with pentobarbital, received a sufficient dose of norepinephrine to increase arterial pressure but not sufficient to cause contraction of the nictitating membrane. Arterial pressure was measured at the carotid immediately after administration of the dose of norepinephrine. After this, increasing doses of Compound 1 in aqueous solution were administered by intraveneous route every 30 minutes. After each dose of Compound 1, a further dose of norepinephrine was given and the following parameters were recorded: the increase in arterial pressure, the contractile reaction of the nictitating membrane due to exogenous norepinephrine as well as the contractile reaction of this membrane induced by the release of norepinephrine provoked by the sub-maximum electric stimulation of the cervical sympathetic nerve.

The results listed hereunder were recorded with Compound 1 and amantadine:

Table VI

|  | Cumulative doses in mg/kg | Increase in arterial pressure in mm Hg after injection of norepinephrine | Contractile reaction of the nictitating membrane (in mm*) | |
|---|---|---|---|---|
|  |  |  | Without electric stimulation | With electric stimulation |
| Compound 1 | 0 | 26 | 0 | 17 |
|  |  | 18 | 0 | 15 |
|  | 1 | 25 | 0 | 16 |
|  | 3 | 29 | 0 | 17 |
|  | 5 | 25 | 0 | 16 |
|  | 10 | 22 | 0 | 12 |
| Amantadine | 0 | 28 | 0 | 20 |
|  | 0.1 | 29 | 0 | 20 |
|  | 1 | 35 | 3 | 20 |
|  | 3 | 35 | 4.4 | 16 |
|  | 5 | 59 | 5.9 | 10 |
|  | 10 | 57 | 7.5 | 4 |

*The mm express the elevation of the contraction registered on a graph.
These results show that Compound 1 does not potentiate the effects either of exogenous norepinephrine or of endogenous norepinephrine.

Amantadine, on the other hand, potentiates exogenous norepinephrine from 1 mg/kg, since it increases the intensity and duration of the hypertensive effects of this amine and, after it has been administered, a dose of norepinephrine which would otherwise have no effect on the membrane provokes, on the contrary, a contractile reaction on the part of the latter.

Furthermore, amantadine itself stimulates the contractile reaction of the nictitating membrane but does not potentiate the effects of the electric stimulation. On the contrary, amantadine shows ganglioplegic properties from 5 mg/kg.

It will be appreciated that for therapeutic use the compounds of the invention will normally be administered in the form of a pharmaceutical or veterinary composition in a dosage unit form appropriate to the required mode of administration, the composition comprising as active ingredient a compound of the invention in association with a pharmaceutical carrier or excipient therefor. For oral administration, the composition may take the form of, for example, a coated or uncoated tablet, a hard- or soft-gelatin capsule, a suspension or a syrup. The composition may alternatively take the form of a suppository for rectal administration, or of a solution or suspension for parenteral administration.

When in dosage unit form the composition may contain from 5 to 50 mg, preferably from 5 to 10 mg of the active ingredient per dosage unit for oral administration, from 5 to 50 mg of the active ingredient per dosage unit for rectal administration, or from 1 to 10 mg of the active ingredient per dosage unit for parenteral administration.

The therapeutic compositions of the invention will be prepared by associating at least one of the compounds of formula I or a pharmaceutically acceptable acid addition salt thereof with at least one appropriate carrier or excipient therefor. Examples of suitable carriers or excipients are talc, magnesium stearate, milk sugar, saccharose, carboxymethylcellulose, starches, kaolin, levilite and cocoa butter.

The following Examples illustrate the preparation of the compounds of the invention together with a suitable therapeutic composition:

EXAMPLE 1

Preparation of 1,1-di-n-propyl-n-butylamine hydrochloride or tri-n-propylmethylamine hydrochloride.

a. 1,1-Di-n-propyl-n-butylisocyanate

In a 2-liter three-necked flask fitted with a water condenser, a mechanical stirrer, a thermometer and a dropping-funnel were placed 144 g of sodium hydroxide in tablet form and 1200 ml of water. The solution was cooled to 5° C and, under stirring, 48 ml of bromine were slowly added. The operation of adding the bromine lasted two hours and then, at a temperature of 0° C, 111 g of 2,2-di-n-propyl-valeramide were added to the yellowish-green solution. Stirring of the mixture was maintained at about 0° C for 4 hours. The oily phase was then extracted with three fractions of ether each of 300 ml and the ethereal phase was washed twice with 100 ml of water, dried over magnesium sulphate and evaporated under vacuum. The light yellow oil so obtained was distilled under reduced pressure of 5 mmHg.

In this manner 105 g of colourless 1,1-di-n-propyl-n-butylisocyanate were obtained.

B.P. 78°–79° C under 5mmHg. Yield: 95%

By following the same procedure as that described hereabove but using the appropriate starting-products, the compounds hereunder were prepared:

| Compounds | Boiling point ° C |
|---|---|
| 1,1-Di-n-butyl-n-pentylisocyanate | 92–93 (0.5 mmHg) |
| (Yield : 80%) |  |
| 1-n-Propyl-1-isopropyl-n-butylisocyanate | 97 (15 mmHg) | b. 1,1-Di-n-propyl-n-butylamine hydrochloride

Into a three necked flask equipped with a mechanical stirrer, a dropping-funnel, a thermometer and a condenser, were introduced 200 ml of water and 90 ml of concentrated hydrochloric acid (d=1.19). The acid solution was heated to 90° C and then, under vigorous stirring, 105 g of 1,1-di-n-propyl-n-butylisocyanate, prepared as previously described, were slowly added. The operation of addition lasted one hour after which the reaction medium was heated for a further 4 hours at a temperature between about 95° and 100° C. The mixture was then cooled to about 0° C and the colourless crystals so obtained were filtered off dried by exposure to the air and then in a dessicator in the presence of potassium hydroxide. In this manner, 99 g of 1,1-di-n-propyl-n-butylamine hydrochloride were isolated in the form of a white crystalline powder.

The product does not melt but sublimates from 220° C.

Yield: 90%.

By following the same procedure as that described hereabove but using the appropriate starting-products, the compounds hereunder were obtained:

| Compound |  |
|---|---|
| 1,1-Di-n-butyl-n-pentylamine hydrochloride | M.P. 68.1° C |
| (Yield : 63%) |  |
| 1-Ethyl-1-n-propyl-n-butylamine | 180° C |

-continued

| Compound | |
|---|---|
| hydrochloride | (sublimation) |
| 1-Ethyl-1-isobutyl-n-butylamine hydrochloride | 230° C (sublimation) |
| 1-n-Propyl-1-isobutyl-n-butylamine hydrochloride | M.P. 260° C |
| 1-Ethyl-1-n-propyl-n-pentylamine hydrochloride | M.P. 230° C (decomposition) |
| 1-n-Propyl-1-isopropyl-n-butylamine hydrochloride | M.P. 260° C (decomposition) |

EXAMPLE 2

Preparation of 1,1-di-n-propyl-n-butylamine acid fumarate

To a solution of 1.16 g (0.01 mol) of fumaric acid in 20 ml of acetone, were slowly added 1.57 g (0.01 mol) of 1,1-di-n-propyl-n-butylamine ($n_D^{21}$= 1.4349) dissolved in 10 ml of acetone, this amine having being prepared from its hydrochloride and a 30% aqueous solution of sodium hydroxide. The mixture was stirred for one hour and then the crystals which formed were suction-filtered, washed with acetone and dried under vacuum.

In this manner, 1,1-di-n-propyl-n-butylamine acid fumarate was obtained in the form of a white powder.
M.P. 216° C with sublimation
Yield: 100%

EXAMPLE 3

Preparation of 1-n-propyl-1-isobutyl-n-butylamine hydrochloride a. 1-n-Propyl-1-isobutyl-n-butanol Into a 250 ml three-necked flask equipped with a mechanical stirrer a nitrogen inlet, a dropping-funnel and a thermometer, were introduced under nitrogen atmosphere 2.8 g (0.2 mol) of lithium in small portions and 100 ml of anhydrous and purified tetrahydrofuran. The suspension of lithium in tetrahydrofuran was cooled to −20° C and then while stirring a mixture of 22.8 g (0.2 mol) of di-n-propylketone and 30 g (0.2 mol plus a 10% excess) of isobutyl bromide were slowly added. The operation of addition lasted about 3 hours during which time a temperature of about −20° C was maintained. The solution was allowed to stand for about 12 hours at room temperature and then concentrated. The oil so obtained was taken up in water, extracted with ether and distilled under reduced pressure.

In this manner, 21 g of 1-n-propyl-1-isobutyl-n-butanol were obtained in the form of a clear liquid which was slightly yellow.
B.P. 74°–76° C under 5 mmHg.
Yield: about 60%

Following the same procedure as that described above but using the appropriate starting-products, the compounds listed hereunder were prepared:

| Compound | Boiling point ° C |
|---|---|
| 1,1-Diethyl-n-butanol (Yield : 50%) | 62 (15 mmHg) |
| 1-Ethyl-1-n-propyl-n-butanol (Yield : 35%) | 178–179 (760 mmHg) |
| 1-Ethyl-1-isobutyl-n-butanol (Yield : 40%) | 78–79 (15 mmHg) |
| 1,1-Di-n-propyl-n-butanol (Yield : 60%0 | 78–80 (0.15 mmHg) |
| 1-n-Propyl-1-isopropyl-n-butanol | 81 (15 mmHg) |
| 1-n-Propyl-1-tert-butyl-n-butanol | 90–92 (14 mmHg) |
| 1,1-Dimethyl-n-octanol (Yield : 45%) | 93–95 (13 mmHg) |

-continued

| Compound | Boiling point ° C |
|---|---|
| 1,1,3-Trimethyl-n-heptanol (Yield : 60%) | Decomposition |
| 1,1-Dimethyl-3-ethyl-n-hexanol (Yield : 30%) | Decomposition |
| 1,3-Dimethyl-1-ethyl-n-hexanol (Yield : 35%) | Decomposition |
| 1,3-Dimethyl-1-n-propyl-n-pentanol (Yield : 46%) | Decomposition |
| 1-Methyl-1-isobutyl-n-pentanol Yield : 33%) | Decomposition |
| 1-Methyl-1-n-propyl-n-hexanol (Yield : 30%) | Decomposition |
| 1,1-Diisobutyl-n-butanol (Yield : 60%) | 75–76 (4 mmHg) |
| 1-Ethyl-1-n-propyl-n-pentanol (Yield : 35%) | 87 (11 mmHg) | b. 1-n-Propyl-1-isobutyl-n-butylamine hydrochloride

Into a 250 ml three-necked flask equipped with a mechanical stirrer, a dropping-funnel, a condenser and a dip thermometer, were introduced 6.5 g (0.1 mol) of dry potassium cyanide in powder form, 14.4 g(0.083 mol) of 1-n-propyl-1-isobutyl-n-butanol and 12 ml of acetic acid. While stirring, a mixture of 25 g of concentrated sulphuric acid (d= 1.83) and 12 ml of acetic acid was slowly added. The operation of addition lasted about 2 hours during which time a temperature of about 50° C was maintained. The reaction mixture was heated to 70° C for 2 hours and was then slowly poured into 100 ml of iced water. After this, it was neutralized with a 20% aqueous solution of sodium hydroxide and extracted with ether. The ether was evaporated out and an oil comprising N-formylated 1-n-propyl-1-isobutyl-n-butylamine was collected.

The N-formylated amine thus obtained was reflux for 2 hours in the presence of 20 ml of concentrated hydrochloric acid. While cooling, the hydrochloride of this amine crystallized. It was then filtered off and washed with acetone.

In this manner, 11 g of 1-n-propyl-1-isobutyl-n-butylamine hydrochloride was collected in the form of a white powder.
M.P.>260° C with decomposition without melting at about 280° C.
Yield: 64%

In a thin layer chromatographic assay performed on silicagel plates (Merck HF 254) using a system of solvents comprising 79 parts of benzene, 14 parts of methanol and 7 parts of acetic acid and with iodine as revealing agent, a Rf of 0.6 was recorded.

Following the same procedure as that described hereabove but using the appropriate starting-products, the compounds listed hereunder were prepared. The Rf value given for each of these compounds was determined in a thin layer chromatographic assay using the same support, the same system of solvents and the same revealing agent as those mentioned in the Example hereabove described:

| Compound | |
|---|---|
| 1,1-Diethyl-n-propylamine hydrochloride (Yield : 40%) Rf = 0.49 | 210° C (sublimation) |
| 1,1-Di-n-propyl-n-butylamine hydrochloride | 220° C (sublimation) |
| 1,1-Diethyl-n-butylamine hydrochloride (Yield : 60%) Rf = 0.59 | M.P. > 300° C |
| 1-Ethyl-1-n-propyl-n-butylamine | 180° C |

| Compound | |
|---|---|
| hydrochloride (Yield : 25%) Rf = 0.64 | (sublimation) |
| 1-Ethyl-1-isobutyl-n-butylamine hydrochloride (Yield : 30%) Rf = 0.60 | 230° C (sublimation) |
| 1,1-Dimethyl-n-octylamine hydrochloride (Yield : 45%) Rf = 0.65 | M.P. 111.8° C |
| 1,3-Dimethyl-1-ethyl-n-hexylamine hydrochloride Rf = 0.56 | M.P. 133.3° C |
| 1-Methyl-1-n-propyl-n-hexylamine hydrochloride (Yield : (60%) Rf = 0.60 | M.P. 174.7° C |
| 1-n-Propyl-1-isopropyl-n-butylamine hydrochloride | M.P. 260° C (Decomposition) |
| 1-Ethyl-1-n-propyl-n-pentylamine hydrochloride (Yield : 30%) Rf = 0.60 | M.P. 230° C (Decomposition) |

EXAMPLE 4

Preparation of 1,1-dimethyl-3-ethyl-n-hexylamine acid fumarate

To a solution of 1.74 g(0.015 mol) of fumaric acid in 300 ml of acetone were slowly added 2.3 g (0.015 mol) of 1,1-dimethyl-3-ethyl-n-hexylamine, prepared as previously described in 40 ml of acetone. The mixture was stirred for 3 hours and the fumarate which crystallized was filtered off, washed with acetone and dried.

In this manner, 2 g of 1,1-dimethyl-3-ethyl-n-hexylamine acid fumarate were obtained in the form of colourless crystals.

M.P. 160.6° C
Yield: 50%

In a thin layer chromatographic assay performed on silicagel plates (Merck HF 254) using a system of solvents comprising 79 parts of benzene, 14 parts of methanol and 7 parts of acetic acid and with iodine as revealing agent, a Rf of 0.56 was recorded.

By following the same procedure as that described above but using the appropriate starting-products, the compounds listed hereunder were prepared.

The Rf value given for each of these compounds was determined in a thin layer chromatographic assay using the same support, the same system of solvents and the same revealing agent as those mentioned in the Example hereabove described:

| Compound | |
|---|---|
| 1,1,3-Trimethyl-n-heptylamine acid fumarate Rf = 0.54 | M.P. 140° C |
| 1-n-Propyl-1-tert-butyl-n-butylamine acid fumarate | 180° C (sublimation) |
| 1,3-Dimethyl-1-n-propyl-n-pentylamine acid fumarate Rf = 0.56 | M.P. 114.4° C |
| 1,1-Diisobutyl-n-butylamine acid fumarate Rf = 0.66 | M.P. 179° C |

EXAMPLE 5

Preparation of 1-methyl-1-isobutyl-n-pentylamine neutral fumarate a. 1-Methyl-1-isobutyl-n-pentylamine 1-Methyl-1-isobutyl-n-pentylamine in free base form was first prepared by reacting a 30% aqueous solution of sodium hydroxide with 1-methyl- 1-isobutyl-n-pentylamine hydrochloride.

The free base so obtained was then extracted with ether.

b. 1-Methyl-1-isobutyl-n-pentylamine neutral fumarate

While stirring, the amine in free base form so obtained was slowly added to a solution of 2.32 g (0.02 mol) of fumaric acid in 300 ml of acetone. The fumarate slowly crystallized. Stirring was maintained for a further hour and the crystals which formed were filtered off, washed with acetone and dried.

In this manner, 3.1 g of 3.1 g of 1-methyl-1-isobutyl-n-pentylamine neutral fumarate were obtained in the form of colourless crystals.

M.P. 198.4° C
Yield: 70%

Rf = 0.58 (in a thin layer chromatographic assay using the same solvents and revealing agent as in Examples 2 and 3 above).

EXAMPLE 6

Preparation of 1-ethyl-1-n-propyl-n-pentylamine hydrochloride a. 2-Ethyl-2-n-propyl-hexanoic acid Into a three-necked flask fitted with a mechanical stirrer, a thermometer and two dropping-funnels, were placed 204 g of 96% sulphuric acid cooled to 5° C and 4 ml of formic acid. While maintaining the mixture at a temperature of about 10° C, 23g (0.5 mol) of formic acid and 15.8 g (0.1 mol) of 1 -ethyl-1-n-propyl-n-pentanol in 100 ml of pentane were simultaneously added. The operation of addition lasted 40 minutes after which the reaction mixture was allowed to return to roomtemperature in 2 hours. The mixture was poured onto 100 g of crushed ice and the acid was extracted with ether. The acid was purified by preparing its sodium salt with a 20% aqueous solution of sodium hydroxide. The aqueous phase was acidified with 50% hydrochloric acid and extracted with ether.

The organic fraction was then dried over magnesium sulphate and concentrated under vacuum.

In this manner, 2-ethyl-2-n-propyl-hexanoic acid was obtained in the form of a colourless liquid.

B.P. 130–132° C under 20 mmHg
Yield: about 20%

Using the same method as that described above, the following compound was prepared:

| Compound | B.P. |
|---|---|
| 2-Ethyl-2-n-propyl-pentanoic acid | 122° C (12 mmHg) | b. 1-Ethyl-1-n-propyl-n-pentylamine

Into a three-necked flask equipped with a mechanical stirrer and a condenser, were introduced 70 ml of chloroform, 18 ml of concentrated sulphuric acid (d= 1.83) and 11g (0.06 mol) of 2-ethyl-2-n-propyl-hexanoic acid prepared as described above. The mixture was heated to 50° C and while stirring 7.5 g of sodium azide in powder form were added. The operation of addition lasted 90 minutes after which the reaction mixture was heated to 50° C for 2 hours. The mixture was then neutralized with a 40% aqueous solution of sodium hydroxide previously cooled to 0° C. The amine was extracted with ether and the ethereal phase was washed with water and dried over magnesium sulphate. The ether was evaporated out under vacuum and the oil so obtained was taken up in dry ether, which provided 1-ethyl-1-n-propyl-n-pentylamine in free base form.

Using the same method as that described above, the following compound was prepared:

| Compound | B.P. |
|---|---|
| 1,1-di-n-propyl-n-butylamine | 190.5–195° C (742 mm Hg) | c. 1-Ethyl-1-n-propyl-n-pentylamine hydrochloride

The hydrochloride of the amine, previously obtained, was precipitated by bubbling dry gaseous hydrochloric acid through the solution of the said amine.

In this manner, 1-ethyl-1-n-propyl-n-pentylamine hydrochloride was obtained in the form of colourless crystals which sublimated from 200° C.

Yield: 45%

By following the same procedure as that described above, the following compounds were prepared:

| Compound | |
|---|---|
| 1,1-Di-n-propyl-n-butylamine hydrochloride | 220° C (sublimation) |
| 1-Ethyl-1-n-propyl-n-butylamine hydrochloride | 180° C (sublimation) |
| 1-Ethyl-1-isobutyl-n-butylamine hydrochloride | 230° C (sublimation) |
| 1-n-Propyl-1-isobutyl-n-butylamine hydrochloride | M.P. 260° C |
| 1-n-Propyl-1-isopropyl-n-butylamine hydrochloride | M.P. 260° C (decomposition) |
| 1,1-Di-n-propyl-3-butyn-1-ylamine hydrochloride | 262° C (sublimation and decomposition) |

EXAMPLE 7

Preparation of 1,1-di-(2-propen-1-yl)-3-buten-1-ylamine oxalate a. 1,1-Di-(2-propen-1-yl)-3-buten-1-ylamine (or triallylmethylamine)

Under nitrogen atmosphere, 13.4 g (0.2 mol) of allyl cyanide in 20 ml of dry ether were added to a solution of 0.4 mol of allyl magnesium bromide in 350 ml of ether. The operation of addition lasted one hour while the ether was lightly refluxed. After this, the reaction medium was heated to boiling for 4 hours. After cooling, the mixture was poured into 200 ml of a saturated solution of ammonium chloride. The ethereal phase was separated out, washed with water, dried over magnesium sulphate and evaporated under vacuum. The oil so obtained was distilled under reduced pressure.

In this manner, 14 g of 1,1-di-(2-propen-1-yl)-3-buten-1-ylamine were obtained in the form of a slightly yellow liquid.

B.P. 79–80° C (under 15 mmHg)
Yield: 46%

By following the same procedure as that described above the following compound was prepared:

| Compound | |
|---|---|
| 1,1-Di-n-propyl-n-butylamine | $n_D^{21} = 1.4349$ | b. 1,1-Di-(2-propen-1-yl)-3-buten-1-ylamine oxalate

While stirring, 3g (about 0.02 mol) of 1,1-di-(2-propen-1-yl)-3-buten-1-ylamine, prepared as described above, in 20 ml of ether were added to 2.5 g (about 0.02 mol) of hydrated oxalic acid (2 molecules of hydration water) in 300 ml of ether.

Stirring was maintained for 30 minutes and then the colourless crystals which precipitated were filtered out. The crystals were washed with ether and recrystallized from ethyl acetate.

In this manner, 4 g of 1,1-di-(2-propen-1-yl)-3-buten-1-ylamine oxalate were obtained.

M.P. 96.2° C
Yield: 70%

By following the same procedure as that described above using hydrochloric acid in place of oxalic acid, the following compound was prepared:

| Compound | |
|---|---|
| 1,1-Di-n-propyl-n-butylamine hydrochloride | 220° C (sublimation) |

EXAMPLE 8

Preparation of 1,1-di-n-propyl-2-propyn-1-ylamine hydrochloride a. 1,1-Di-n-propyl-2-propyn-1-ol A 2-litre three-necked flask fitted with a mechanical stirrer, a condenser, a dip tube and a dropping-funnel was placed in a fume cupboard. Into the flask previously cooled in a bath of carbon-dioxide snow in acetone, was introduced 1 liter of liquid ammonia. Acetylene, previously purified by passing through a trap containing carbon-dioxide snow, bubbling in a sulphuric acid solution and drying over caustic potash, was then bubbled through the reaction medium.

To the acetylene solution in ammonia were added 23 g of finely divided sodium. The bubbling of acetylene was maintained for 1 hour after the introduction of the sodium. After that, 114 g (1 mol) of di-n-propyl ketone were added and the acetylene flow was maintained for 1 hour after which 500 ml of ether were added and the mixture was allowed to stand for 12 hours at room-temperature. It was then hydrolysed by adding damp ether followed by crushed ice. After acidification with 10% sulphuric acid, the ethereal phase was separated out, dried over magnesium sulphate and concentrated under reduced pressure.

In this manner, 45 g of 1,1-di-n-propyl-2-propyn-1-ol were collected after distillation, which represents a yield of 32%.

B.P. 68°–70° C b. 1,1-Di-n-propyl-1-chloro-2-propyne

Into a 3-necked flask fitted with a magnetic stirrer, a thermometer and a dropping-funnel, were placed 6.5 g of freshly prepared cuprous chloride, 9.1 g of calcium chloride, 0.020 g of copper-bronze powder and 71 ml of concentrated and iced hydrochloric acid (d = 1.19). While stirring, 23 g of 1,1-di-n-propyl-2-propyn-1-ol, prepared as described above were added to the mixture maintained at 10° C.

The operation of adding the alcohol lasted 30 minutes and then the reaction mixture was allowed to stand for 2 hours at room-temperature. The supernating part of the mixture was decanted into a dropping-funnel and washed with twice 15 ml of concentrated and iced hydrochloric acid and then with three times 20 ml of distilled water. After drying over potassium carbonate, the mixture was distilled to give the desired product.

In this manner, 17 g of 1,1-di-n-propyl-1-chloro-2-propyne in the form of a limpid and colourless liquid were obtained which represents a yield of 65%.

B.P. 63°–65° C under 14 mm Hg.

c. 1,1-Di-n-propyl-2-propyn-1-ylamine

To a suspension of sodium amide in liquid ammonia, prepared from 6.9 g of sodium and 250 ml of liquid ammonia, were added 17 g of 1,1-di-n-propyl-1-chloro-2-propyne in 50 ml of anhydrous ethyl ether. The operation of adding the chlorinated derivative lasted one hour. Stirring of the mixture was maintained for 2 hours and then 300 ml of anhydrous ethyl ether were added.

The reaction medium was allowed to stand for 12 hours after which the ammonia was evaporated off and 100 g of crushed ice were added. The ethereal phase was separated out and the basic phase was extracted with 300 ml of a 10% aqueous solution of hydrochloric acid. The amine was recovered by adding concentrated and iced caustic soda and again extracting with ether.

In this manner, 1,1-di-n-propyl-2-propyn-1-ylamine was obtained in the form of its free base.

By following the same method as that described above, the compounds listed below were prepared:

| Compound | |
|---|---|
| 1,1-Dimethyl-2-propyn-1-ylamine | M.P. 18° C |
| 1,1-Diethyl-2-propyn-1-ylamine | B.P. 71–72° C (90 mm Hg) | d. 1,1-Di-n-propyl-2-propyn-1-ylamine hydrochloride

The ethereal solution of amine previously obtained was dried over magnesium sulphate and the hydrochloride of this amine was then precipitated by bubbling dry gaseous hydrochloric acid. The crystals so obtained were separated out and dried in a dessicator in the presence of caustic potash.

In this manner, 12 g of 1,1-di-n-propyl-2-propyn-1-ylamine hydrochloride were obtained in the form of colourless crystals, which represents a yield of 68%.

M.P. 200° C (with decomposition).

EXAMPLE 9

Preparation of 1,1-diethyl-2-pentyn-1-ylamine hydrochloride a. 1,1-Diethyl-2-pentyn-1-ylamine Into a 3 necked-flask fitted with a mechanical stirrer, a vertical condenser and a dropping-funnel, was prepared a suspension of sodium amide from 150 ml of liquid ammonia, 2.4 g of sodium and some crystals of ferric nitrate. To this suspension, was added, in 30 minutes, a solution of 11 g of 1,1-diethyl-2-propyn-1-ylamine, prepared as previously described, and 20 ml of anhydrous ethyl ether. When the operation of addition was finished, the stirring of the mixture was maintained for 30 minutes and a solution of 15 g of dry ethyl bromide in 30 ml of anhydrous ethyl ether was introduced drop-by-drop into the reaction mixture. The operation of adding the ethyl bromide lasted 1 hour, after which stirring of the mixture was maintained for 4 hours. The reaction medium was then allowed to stand for 12 hours so that the ammonia could evaporate and 50 g of crushed ice were added. The ethereal phase was separated out, dried over magnesium sulphate and then evaporated out under reduced pressure.

In this manner, 8 g of 1,1-diethyl-2-pentyn-1-ylamine were obtained, after distillation, in the form of a colourless liquid.

B.P. 62°–63° C under 15 mm Hg.

Yield: 57%

By following the same procedure as that described above but using the appropriate starting-products, the following compounds was prepared:

| Compound | B.P. |
|---|---|
| 1,1-Di-n-propyl-2-pentyn-1-ylamine (Yield : 55%) | 92–94° C (15 mm Hg) | b. 1,1-Diethyl-2-pentyn-1-ylamine hydrochloride

The hydrochloride of the amine previously obtained was prepared by treating an anhydrous ethereal solution of this amine with dry gaseous hydrochloric acid. By evaporating the ether and drying the crystals so obtained in a dessicator and in the presence of caustic potash, 1,1-diethyl-2-pentyn-1-ylamine hydrochloride was obtained in the form of a white powder.

M.P. 85° C

Yield: 100%

By following the same procedure as that described above, the following compound was prepared:

| Compound | M.P. |
|---|---|
| 1,1-Di-n-propyl-2-pentyn-1-ylamine hydrochloride (Yield : 100%). | 118° C |

EXAMPLE 10

Preparation of 1,1-diethyl-2-penten-1-ylamine hydrochloride

In 40 ml of heptane, 3.5 g of 1,1-diethyl-2-pentyn-1-ylamine were hydrogenated in the presence of 50 mg of a Lindlar catalyst (catalyst formed from palladium, sodium carbonate and lead oxide). The addition of hydrogen on the triple bond was facilitated by maintaining the mixture under stirring and heating it to a temperature of about 50° C. The absorption of 560 cm$^3$ of hydrogen was achieved in 90 minutes. After evaporating the solvent, the desired hydrochloride was isolated by adding dry gaseous hydrochloric acid. The crystals so obtained were dried in a dessicator in the presence of caustic potash.

In this manner, 1,1-diethyl-2-penten-1-ylamine hydrochloride was obtained in the form of a white powder.

M.P. 200° C with sublimation.

Yield: 100%

By following the same procedure as that described above, the following compound was prepared:

| Compound | |
|---|---|
| 1,1-Di-n-propyl-2-penten-1-ylamine (Yield : 100%) | 200° C (sublimation) |

EXAMPLE 11

A hard-gelatin capsule containing the following ingredients was prepared in accordance with known pharmaceutical techniques:

| Ingredients | mg |
|---|---|
| 1,1-Di-n-propyl-n-butylamine hydrochloride | 5 |
| Milk sugar | 45 |
| | 50 |

We claim:
1. 1,1-Di-n-propyl-n-butylamine acid fumarate.

* * * * *

UNITED STATES PATENT OFFICE
CERTIFICATE OF CORRECTION

Patent No. 4,026,925           Dated May 31, 1977

Inventor(s) Charles Pigerol, Pierre Eymard, Jean-Claude Vernieres, and Jean-Pierre Werbenec It is certified that error appears in the above-identified patent and that said Letters Patent are hereby corrected as shown below:

Column 1, below the line reading "[21] Appl. No.: 577,732"

insert the following:

-- [30] Foreign Application Priority Data
       May 20, 1974 Belgium .....P.V.O./144,519 --

Signed and Sealed this

Thirteenth Day of June 1978

[SEAL]

Attest:

RUTH C. MASON
Attesting Officer

DONALD W. BANNER
Commissioner of Patents and Trademarks